United States Patent [19]

Nelson

[11] 4,203,924

[45] May 20, 1980

[54] 2-DECARBOXY-2-HYDROXYMETHYL-DEOXY-9,10-DIDEHYDRO-PGD$_2$ ANALOGS

[75] Inventor: Norman A. Nelson, Galesburg, Mich.

[73] Assignee: The Upjohn Company, Kalamazoo, Mich.

[21] Appl. No.: 784,981

[22] Filed: Apr. 6, 1977

Related U.S. Application Data

[62] Division of Ser. No. 647,369, Jan. 28, 1976, Pat. No. 4,032,576.

[51] Int. Cl.$^2$ .............................................. C07C 49/56
[52] U.S. Cl. ..................................... 568/379; 568/380
[58] Field of Search ..................................... 260/586 R

[56] References Cited

FOREIGN PATENT DOCUMENTS

2323127  11/1973  Fed. Rep. of Germany ........... 260/586

*Primary Examiner*—Robert Gerstl
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

15 Claims, No Drawings

2-DECARBOXY-2-HYDROXYMETHYL-DEOXY-9,10-DIDEHYDRO-PGD₂ ANALOGS

The present application is a divisional application of Ser. No. 647,369 filed Jan. 28, 1976, now issued as U.S. Pat. No. 4,032,576 on June 28, 1977.

The present invention relates to prostaglandin analogs, for which the essential material constituting disclosure therefor is incorporated by reference here from Serial No. 647,369, filed January 8, 1976, now pending issuance as a United States Patent.

I claim:

1. A prostaglandin analog of the formula

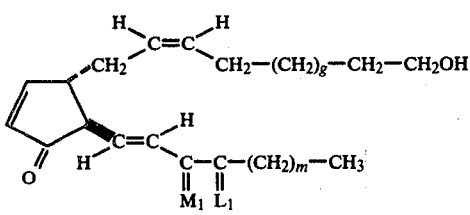

wherein $M_1$ is

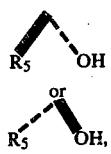

or

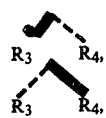

wherein
  $R_5$ is hydrogen or methyl;
  wherein $L_1$ is

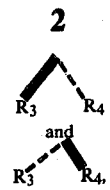

or a mixture of wherein $R_3$ and $R_4$ are hydrogen, methyl or fluoro, being the same or different, with the proviso that one of $R_3$ and $R_4$ is methyl only when the other is hydrogen or methyl;
  wherein g is one, 2, or 3; and
  wherein m is one to 5, inclusive;
  with the proviso that at least one of $R_3$, $R_4$, and $R_5$ is methyl or at least one of $R_3$ and $R_4$ is fluoro.

2. A compound according to claim 1, wherein m is one or 2.

3. A compound according to claim 1, wherein m is 4 or 5.

4. A compound according to claim 1, wherein m is 3.

5. A compound according to claim 4, wherein g is one.

6. A compound according to claim 5, wherein at least one of $R_3$ and $R_4$ is fluoro.

7. A compound according to claim 6, wherein $R_3$ and $R_4$ are both fluoro.

8. A compound according to claim 7, wherein $R_5$ is hydrogen.

9. 2-Decarboxy-2-hydroxymethyl-16,16-difluoro-9-deoxy-9,10-didehydro-PGD₂, a compound according to claim 8.

10. A compound according to claim 5, wherein at least one of $R_3$ and $R_4$ is methyl.

11. A compound according to claim 10, wherein $R_3$ and $R_4$ are both methyl.

12. A compound according to claim 11, wherein $R_5$ is hydrogen.

13. 2-Decarboxy-2-hydroxymethyl-16,16-dimethyl-9-deoxy-9,10-didehydro-PGD₂, a compound according to claim 12.

14. A compound according to claim 5, wherein $R_3$ and $R_4$ are hydrogen and $R_5$ is methyl.

15. 2-Decarboxy-2-hydroxymethyl-15-methyl-9-deoxy-9,10-didehydro-PGD₂, a compound according to claim 14.

* * * * *

UNITED STATES PATENT OFFICE
CERTIFICATE OF CORRECTION

Patent No. 4,203,924            Dated 20 May 1980

Inventor(s) Norman A. Nelson

It is certified that error appears in the above-identified patent and that said Letters Patent are hereby corrected as shown below:

The title should read -- 2-DECARBOXY-2-HYDROXYMETHYL-9-DEOXY-9,10-DIDEHYDRO-$PGD_2$ ANALOGS -- instead of as appears in the patent.

Column 1, lines 12-13, "now pending issuance as a United States Patent." should read -- now United States Patent 4,032,576. --

Signed and Sealed this

Sixth Day of January 1981

[SEAL]

Attest:

SIDNEY A. DIAMOND

Attesting Officer      Commissioner of Patents and Trademarks